(12) United States Patent
Kim et al.

(10) Patent No.: US 7,135,199 B2
(45) Date of Patent: Nov. 14, 2006

(54) ALCOHOL-FERMENTED FOOD OR PHARMACEUTICAL COMPOSITION FOR PREVENTION OF OBESITY AND PROCESS FOR PREPARATION THEREOF

(75) Inventors: Hyung-Min Kim, 103-1504 Samsung Raemian Apt., 425 Imun2-dong, Dongdaemun-gu, Seoul (KR) 130-716; Seung-Heon Hong, Iksan (KR)

(73) Assignee: Hyung-Min Kim, Seoul (KR)

( * ) Notice: Subject to any disclaimer, the term of this patent is extended or adjusted under 35 U.S.C. 154(b) by 0 days.

(21) Appl. No.: 10/967,434

(22) Filed: Oct. 18, 2004

(65) Prior Publication Data

US 2006/0083797 A1    Apr. 20, 2006

(51) Int. Cl.
*A01N 65/00* (2006.01)
(52) U.S. Cl. ...................................... 424/725
(58) Field of Classification Search ................ 424/725
See application file for complete search history.

(56) References Cited

OTHER PUBLICATIONS

BM Balsiger, MM Murr, JL Poggio, and MG Sarr, "Bariatric surgery. Surgery for weight control in patients with morbid obesity." Abstract. Med Clin North Am. Mar. 2000:84(2):477-89.
LB Oscai, WC Miller, and DA Arnall, "Effects of dietary sugar and of dietary fat on food intake and body fat content in rats." Abstract. Growth, 1987 Spring:51(1):64-73.
R. James Barnard, Christian K.. Roberts, Shira M. Varon, and Joshua J. Berger, "Diet-induced insulin resistance precedes other aspects of the metabolic syndrome." Dept. of Physiological Science, University of California, Los Angeles, California 90095, The American Physiological Society, 1998, pp. 1311-1315.
LB Oscai, MM Brown, and WC Miller, "Effect of dietary fat on food intake, growth and body composition in rats." Abstract. Growth. 1984 Winter:48(4):415-24.
WC Miller, MG Niederpruem, JP Wallace, and AK Lindeman, "Dietary fat, sugar, and fiber predict body fat content." Abstract. J. Am. Diet Assoc. Jun. 1994:94(6):612-5.

*Primary Examiner*—Michael Meller
(74) *Attorney, Agent, or Firm*—Gates & Cooper LLP

(57) ABSTRACT

The present invention relates to an extract of mixed herb medicine, and a pharmaceutical composition for the prevention and treatment of obesity containing the extract as an effective ingredient or health food containing the same, more precisely, an extract of mixed herb medicine extracted from the mixture of cassia seeds (*Cassia obtusifolia* L.), green tea (*Thea sinensis* L.), eucommia bark (*Eucommia ulmoides* Oliver), garlic (*Allium sativum* var. *pekinense*), hawthorn (*Crataegus Pinnatifida* Bunge), fresh pine needle (*Pinus densiflora* Siebold et Zuccarini) and wormwood (*Artemisia capillaris* Thunberg) using water or aqueous alcohol solution, a pharmaceutical composition for the prevention and treatment of obesity containing the above extract and a fermented extract extracted after adding rice, malt and yeast to the above mixture, or health food containing the same. The extract of the present invention can be effectively used for the prevention and the treatment of obesity by inhibiting weight gain by high-fat diet, lowering blood cholesterol and decreasing neutral fat (triglyceride).

6 Claims, 4 Drawing Sheets

ALCOHOL-FERMENTED FOOD OR PHARMACEUTICAL COMPOSITION FOR PREVENTION OF OBESITY AND PROCESS FOR PREPARATION THEREOF

BACKGROUND OF THE INVENTION (a) Field of the Invention

The present invention relates to an extract of mixed herb medicine, and a pharmaceutical composition for the prevention and the treatment of obesity containing the extract as an effective ingredient or health food containing the same, more precisely, an extract of mixed herb medicine extracted from the mixture of cassia seeds (*Cassia obtusifolia* L.), green tea (*Thea sinensis* L.), eucommia bark (*Eucommia ulmoides* Oliver), garlic (*Allium sativum* var. *pekinense*), hawthorn (*Crataegus Pinnatifida* Bunge), fresh pine needle (*Pinus densiflora* Siebold et Zuccarini) and wormwood (*Artemisia capillaris* Thunberg) using water or aqueous alcohol solution, a pharmaceutical composition for the prevention and the treatment of obesity containing the above extract and a fermented extract extracted after adding rice, malt and yeast to the above mixture, or health food containing the same.

(b) Description of the Related Art

The surplus of calorie intake is converted into fat, which is accumulated in many regions of a body especially in hypodermic tissues and in abdominal cavity, causing obesity. Triglyceride is a compound chemically produced by ester bond between glycerine and three molecules of fatty acid. As a neutral fat synthesized from carbohydrate, triglyceride is stored in adipose tissues of an animal, and releases free fatty acids in blood when it is hydrolyzed by a specific enzyme. Triglyceride stored in adipose tissues is decomposed into nonesterified fatty acid (NEFA) and glycerol to be released in blood when an energy source glucose is insufficient. After being used as a substitute energy source, the surplus of nonesterified fatty acid is converted into triglyceride in the liver again. Triglyceride flowing through blood is called endogenous neutral fat. The high accumulation of triglyceride in the adipose tissue closely relates to artherosclerosis, coronary artery diseases, etc.

Obesity means the more accumulation of fat than that required in a body. Thus, a patient with obesity suffers from disorders by biochemical and physiological malfunctions in a body. Obesity is not only a major cause of various diseases such as diabetes mellitus, hyperlipemia, hypertension, coronary artery disease and joint disease, but also is an obstacle to normal social activities.

To alleviate suffering from obesity, efforts have been made to develop weight reducers, appetite inhibitors or fat absorption inhibitors, etc. Recently, products for not only the prevention and treatment of obesity but also the weight control to have a nice appearance are under development. However, there are a variety of problems about such products unfortunately. For example, a diuretic and a laxative, which are commercially obtainable at low prices, might reduce body weight but the weight loss effect is temporary only by reducing moisture in a body, which is far from eliminating the cause of obesity, such as surplus fat. Moreover, overuse of those medicines can even cause dehydration and abnormal heartbeat by the loss of electrolytes. The habitual dosage of those medicines causes side effects such as edema or constipation by lowering the function of excretion. And diet products using an anorexigenic agent for weight control can induce side effects such as hypertension caused by nerve excitation, abdominal pain, hypersensitivity, insomnia, dizziness, etc. Besides, long term administration of a fibrous product, as one of popular diet products, can cause malnutrition because a fibrous product is produced not for losing weight but simply for satiety.

Even after all the hard work to develop a medicine for the prevention and treatment of obesity, a successful result is not in our hands, yet.

Thus, the present inventors have made extensive effort to develop, by using safe food, an effective composition inhibiting obesity without side effects. As a result, the present inventors have completed this invention by developing a novel herb extract having an excellent effect on the treatment of obesity inhibiting effect without such side effects as conventional drugs have.

SUMMARY OF THE INVENTION

It is an object of the invention to provide an extract of a mixture of cassia seeds (*Cassia obtusifolia* L.), green tea (*Thea sinensis* L.), eucommia bark (*Eucommia ulmoides* Oliver), garlic (*Allium sativum* var. *pekinense*), hawthorn (*Crataegus Pinnatifida* Bunge), fresh pine needle (*Pinus densiflora* Siebold et Zuccarini) and wormwood, a pharmaceutical composition for the prevention and treatment of obesity containing the above extract as an effective ingredient and health food containing the same.

Figure 1:
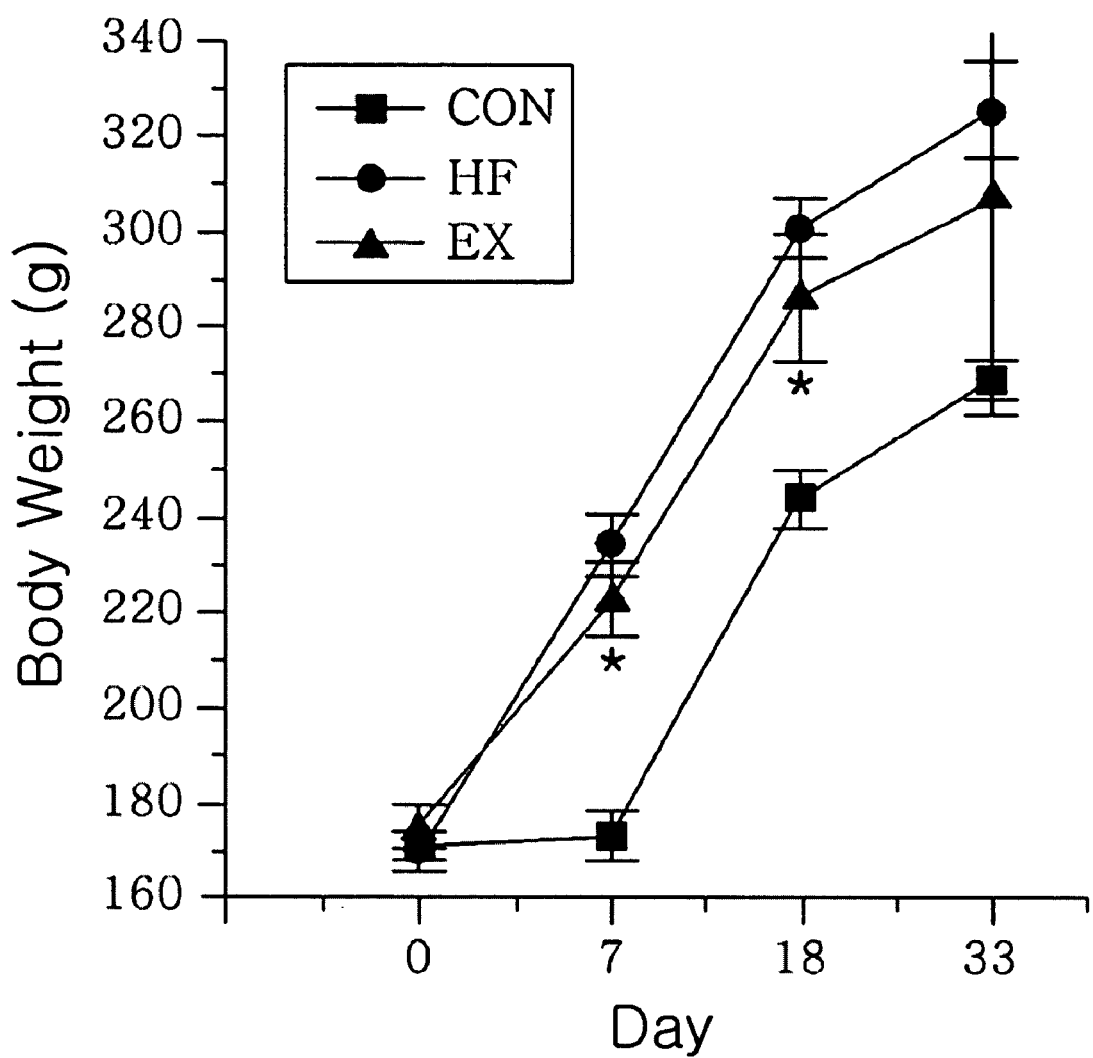
FIG. 1 is a graph showing the weight changes of each rat in a normal diet group, a high fat diet group (control group) and an experimental group fed with high fat diet together with an extract of the present invention, ■: Normal diet group, ●: High fat diet group (control group), ▲: High fat diet+extract of the present invention

CON: Normal diet group,

HF: High fat diet group (control group),

EX: High fat diet+extract of the present invention

DETAILED DESCRIPTION OF THE PREFERRED EMBODIMENTS

To achieve the mentioned-above object, the present invention provides an extract of a mixture of cassia seeds (*Cassia obtusifolia* L.), green tea (*Thea sinensis* L.), eucommia bark (*Eucommia ulmoides* Oliver), garlic (*Allium sativum* var. *pekinense*), hawthorn (*Crataegus Pinnatifida* Bunge), fresh pine needle (*Pinus densiflora* Siebold et Zuccarini) and wormwood (*Artemisia capillaris* Thunberg) extracted by using water or aqueous alcohol solution, or a fermented extract obtained from the above extract after adding rice, malt and yeast.

The present invention also provides a pharmaceutical composition for the prevention and treatment of obesity containing the above extract as an effective ingredient.

The present invention further provides health food for the prevention and treatment of obesity containing the above extract as an effective ingredient.

Hereinafter, the present invention is described in detail.

The present invention provides a herb extract extracted from the mixture of cassia seeds (*Cassia obtusifolia* L.), green tea (*Thea sinensis* L.), eucommia bark (*Eucommia ulmoides* Oliver), garlic (*Allium sativum* var. *pekinense*), hawthorn (*Crataegus Pinnatifida* Bunge), fresh pine needle (*Pinus densiflora* Siebold et Zuccarini) and wormwood using water or acquous alcohol solution.

Cassia seeds used for the present invention are seeds of annual herbal *Cassia obtusifolia* L., which have been used for intestinal regulation, urination and treatment of ophthalmic diseases. Green tea for the invention is young leaves of *Thea sinensis* L., which functions as clear heat, detoxication and urination. Eucommia bark, a bark of *Eucommia ulmoides* Oliver, has antihypertensive and tonic effects. Garlic (*Allium sativum* var. *pekinense*) has effects of health stomach, insecticide and detoxication. Hawthorn, which is a dried fruit of *Crataegus Pinnatifida* Bunge, has activities of stimulating secretion of gastric juice and lowering blood pressure and has antibacterial acitvities. While fresh pine needle (*Pinus densiflora* Siebold et Zuccarini) are very effective for the prevention of lumbago (low back pain), chronic bronchitis and a cold, wormwood (*Artemisia capillaris* Thunberg) is effective for the treatment of infection and jaundice and for the stimulated secretion of bile acid.

It is preferred for the herbal mixture of the present invention to include cassia seeds (*Cassia obtusifolia* L.), green tea (*Thea sinensis* L.), eucommia bark (*Eucommia ulmoides* Oliver), garlic (*Allium sativum* var. *pekinense*), hawthorn (*Crataegus Pinnatifida* Bunge), fresh pine needle (*Pinus densiflora* Siebold et Zuccarini) and wormwood at the ratio of 1–3:0.5–1:2–7:1–3:0.5–1:3–7:3–7 w/w. The above herbal mixture is extracted by using water or acquous alcohol solution.

The mixed ratio of the mentioned-above herbs was determined by repeated experiments. If any herb is added less than the lower limit, pharmacological effects of the component decrease, and if any herb is added more than the upper limit, it drops the pharmacological effects of other components, resulting in decrease of synergism or cooperation of the whole mixture.

The present invention provides an extract which is prepared by hot-water extraction by adding water to the above herb mixture, followed by vacuum-drying thereof.

The present invention also provides an extract which is extracted from the above mixture with acquous alcohol solution and vacuum dried. Acquous alcohol solution used for the invention is selected from a group consisting of 5–100% methyl alcohol and 5–100% ethyl alcohol.

The present invention further provides an extract which is fermented after adding rice, malt and yeast to the above herb extract.

It is preferred that rice, malt and yeast are mixed at the ratio of 20–80:10–40:0–2 w/w before adding to the above herb extract.

The mixture is preferably fermented at 15–30° C. for 5–15 days, which is filtered to separate liquid and solid phases. The liquid phase is heated at 55–60° C. to prepare a medicinal wine.

In order to investigate the effect of an extract of the present invention on the prevention and treatment of obesity, white rats were divided into three groups (normal diet group, control group fed with high fat diet and experimental group fed with high fat diet together with a composition of the present invention) and their weight changes were investigated. An average weight of a control group was higher than that of a normal diet group, but lower than that of an experimental group (see FIG. 1). The results indicate that an extract of the present invention inhibits weight gain effectively. Thus, it is confirmed that the extract of the present invention can control high fat diet induced weight gain successfully.

The lipid contents of serum, such as cholesterol, triglyceride, low-density lipoprotein (LDL) and high-density lipoprotein (HDL), were measured. As a result, the amount of total cholesterol was much increased in a control group than in a normal diet group. And the increased rate of cholesterol of an experimental group was much lower than that of a control group (see FIG. 2). The contents of HDL and LDL were not significantly changed (see FIG. 3). The content of triglyceride was much increased in a control group than in a normal diet group, but the content of triglyceride decreased in an experimental group, comparing to that of a control group (see FIG. 4). The above results indicate that an extract of the present invention excellently inhibits the accumulation of neutral fat (triglyceride). Thus, the lipid content in serum resulting from high fat diet can be effectively controlled by an extract of the present invention.

Therefore, an extract of the present invention can be effectively used for the prevention and treatment of obesity by lowering the concentration of neutral fat to inhibit the accumulation of fat in blood.

The present invention also provides a pharmaceutical composition for the prevention and treatment of obesity containing the above extract as an effective ingredient.

In it preferred to prepare an extract of the present invention in liquid form in the aspect of the best effect, but if necessary, it can be formulated as pills, granules, tablets, capsules or other acceptable forms for administration. But, liquid form is still the most preferable form for an extract of the present invention to contain a required concentration for the best effect.

The extract of the present invention can be administered orally or parenterally and be prepared in general forms of pharmaceutical formulation.

Precisely, the extract of the present invention can be prepared for oral or parenteral administration by being mixed with generally used fillers, extenders, binders, wetting agents, disintegrating agents, diluents such as surfactant, or excipients. Solid formulations for oral administration include tablets, pill, dusting powders and capsules. These solid formulations are prepared by mixing one or more suitable excipients such as starch, calcium carbonate, sucrose or lactose, gelatin, etc. In addition to the simple excipients, lubricants, for example magnesium stearate, talc, etc, can be used. Liquid formulations for oral administration are suspensions, solutions, emulsions and syrups, and the mentioned-above formulations can contain various excipients such as wetting agents, sweeteners, aromatics and preservatives in addition to generally used simple diluents such as water and liquid paraffin. Formulations for parenteral administration include sterilized aqueous solutions, water-insoluble excipients, suspensions, emulsions, freeze drying agents and suppositories. In addition to the active compound or compounds, water insoluble excipients and suspensions can contain, propylene glycol, polyethylene glycol, vegetable oil like olive oil, injectable ester like ethylolate, etc. Suppositories can contain witepsol, macrogol, tween 61, cacao butter, laurin butter, glycerinated gelatin, etc.

The effective dosage of the extract of the present invention, when it is prepared as a medicinal wine by fermentation by the procedure described hereinafter, ranges from 0.5–3.0 ml/kg, and 1–2 ml/kg is more preferable. The administration is carried out once or in the several divided times a day.

In order to prepare a principal extract of the present invention, 50–150 g of cassia seeds (*Cassia obtusifolia* L.), 25–50 g of green tea (*Thea sinensis* L.), 100–350 g of eucommia bark (*Eucommia ulmoides* Oliver), 50–150 g of garlic (*Allium sativum* var. *pekinense*), 25–50 g of hawthorn (*Crataegus Pinnatifida* Bunge), 150–350 g of fresh pine needle (*Pinus densiflora* Siebold et Zuccarini) and 150–350 g of wormwood were all mixed, and 5,000–8,000 ml of water was added thereto. The resulting mixture was heated for 2–4 hours to be concentrated to about 3,000 ml, resulting in an extract. 1–4 kg of steamed rice prepared from rice, 0.2–1 kg of malt and 0–0.1 kg of yeast were mixed homogenously, and then the above extract was added thereto. The mixture solution was fermented at 20–27° C. for 5–10 days, followed by filtering to prepare a medicinal wine. Purified water was then added to the medicinal wine to adjust the volume by 3,000 ml. The composition of the present invention is generally administered in an effective amount of 1.0–2.0 ml/1 kg weight and it is preferred to administer the composition three times a day. For example, in an adult having 60 kg of body weight it is preferred to take every 60–120 ml of the composition in the three divided times a day. The total amount of the composition prepared above is dosed enough for 8–15 days. However, the dosage can be varied according to body weight, age, gender and digestion efficiency of a patient, and severity of a disease. The dosage of the composition in the other form is determined based on the liquid form of the composition, which can be also administered orally or parenterally. Symptoms are relieved 2–3 days after administration although there might be difference of their effects among individuals.

The present invention also provides health food for the prevention and treatment of obesity containing the above extract as an effective ingredient.

When the extract of the present invention is used as food, it is added to food or mixed with other food components together by conventional procedures. A mixing ratio of each effective component is suitably determined according to its use (for prevention, for improving health or for treatment). In general, the extract of the present invention is added to food or beverages by 0.001–50 weight % and more preferably 0.01–5 weight %, based on the weight of raw material. The effective dosage of the extract of the present invention can be determined in accordance with the dosage of the pharmaceutical composition of the present invention. The dose may be reduced for long-term administration to maintain the health but it can be even increased without health problems because the pharmaceutical composition of the present invention is very safe for human.

There is no limitation to food applicable to the extract of the present invention. So, the extract of the present invention can be added to food, such as meat, sausages, bread, chocolate, candies, snacks, cookies, pizza, ramyun, noodles, gums, dairy products including ice cream, soups, beverages, tea, drinks, alcoholic drinks and vitamin complex, etc.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation 1 of a Mixed Herb Extract 5 l of water was added to the mixture of 75 g of cassia seeds (*Cassia obtusifolia* L.), 25 g of green tea (*Thea sinensis* L.), 150 g of eucommia bark (*Eucommia ulmoides* Oliver), 75 g of garlic (*Allium sativum* var. *pekinense*), 30 g of hawthorn (*Crataegus Pinnatifida* Bunge), 150 g of fresh pine needle (*Pinus densiflora* Siebold et Zuccarini) and 150 g of wormwood (*Artemisia capillaris* Thunberg). The resulting mixture was heated for 2.5 hours to concentrate to 3 l, resulting in an herb extract.

EXAMPLE 2

Preparation 2 of a Mixed Herb Extract 1 l of 70% aqueous methanol solution was added to the mixture of 75 g of cassia seeds (*Cassia obtusifolia* L.), 25 g of green tea (*Thea sinensis* L.), 150 g of eucommia bark (*Eucommia ulmoides* Oliver), 75 g of garlic (*Allium sativum* var. *pekinense*), 30 g of hawthorn (*Crataegus Pinnatifida* Bunge), 150 g of fresh pine needle (*Pinus densiflora* Siebold et Zuccarini), and 150 g of wormwood. The resulting mixture was heated at room temperature for 2 days. Then the mixture solution was filtered three times with a filter paper. The filtrate was concentrated under reduced pressure to remove methanol, followed by freeze-drying to eliminate moisture, resulting in a mixed herb extract.

EXAMPLE 3

Preparation 3 of a Mixed Herb Extract 5 l of water was added to the mixture of 75 g of cassia seeds (*Cassia obtusifolia* L.), 25 g of green tea (*Thea sinensis* L.), 150 g of eucommia bark (*Eucommia ulmoides* Oliver), 75 g of garlic (*Allium sativum* var. *pekinense*), 30 g of hawthorn (*Crataegus Pinnatifida* Bunge), 150 g of fresh pine needle (*Pinus densiflora* Siebold et Zuccarini) and 150 g of wormwood. The resulting mixture was heated for 2.5 hours to concentrate to 3 l. 2 kg of steamed rice prepared from rice, 1 kg of malt and 50 g of yeast were mixed homogenously. The above extract was poured to the mixture, which was fermented at 20–25° C. for 7 days. The fermented solution was filtered to separate liquid and solid phases. The liquid phase was heated at 55–60° C., leading to inactivation of enzymes. As a result, a medicinal wine was prepared, whose volume was adjusted to 3,000 ml by adding distilled water.

Manufacturing Example 1

Preparation of Injectable Solutions

The injectable solutions containing 10 mg of the effective ingredient were prepared as follows.

1 g of an extract prepared above, 0.6 g of sodium chloride and 0.1 g of ascorbic acid were dissolved in distilled water to give 100 ml of solution. The resulting solution was poured into a bottle and heated at 120° C. for 30 minutes or filtration for sterilization.

The constituents of the injectable solutions are as follows.

| | |
|---|---|
| Mixed herb extract | 1 g |
| Sodium chloride | 0.6 g |
| Ascorbic acid | 0.1 g |
| Distilled water | Proper amount |

Manufacturing Example 2

Preparation of Syrups

Syrups containing as an effective ingredient an extract of the present invention by 2% (weight/volume) were prepared as follows.

A mixed herb extract, saccharin and glucose were dissolved in 80 ml of warm water. The resulting mixture was cooled down, and a mixture solution of glycerin, flavoring agents, ethanol, sorbic acid and distilled water was added thereto. Distilled water was added to the mixture, making a total volume of 100 ml.

The constituents of the syrups are as follows.

| | |
|---|---|
| Mixed herb extract | 2 g |
| Saccharin | 0.8 g |
| Glucose | 25.4 g |
| Glycerin | 8.0 g |
| Flavoring agent | 0.04 g |
| Ethanol | 4.0 g |
| Sorbic acid | 0.4 g |
| Distilled water | Proper amount |

Manufacturing Example 3

Preparation of Beverages

Beverages containing a mixed herb extract of the present invention as an effective ingredient were prepared as follows.

| | |
|---|---|
| Honey | 522 mg |
| Thioctic acid amide | 5 mg |
| Nicotinic acid amide | 10 mg |
| Sodium riboflavin hydrochloric acid | 3 mg |
| Pyridoxine hydrochloride | 2 mg |
| Inositol | 30 mg |
| Ortho acid | 50 mg |
| Mixed herb extract | 0.48~1.28 mg |
| Water | 200 ml |

Beverages were prepared by the conventional method based on the above-mentioned components and contents.

Experimental Example 1

Weight Loss Effect

White rats of male SD (Sprague-Dawley) line were used in this experiment. Test animals were divided into three groups (8 rats per group) which were a normal diet group, a high fat diet group (control) and an experimental group fed with high fat diet together with a composition of the present invention. Conventional feed was given to a normal diet group. The diet for a control group was prepared to give fat calorie as much as 40% of the total calorie and cholesterol was added by 0.05%. The diet for an experimental group was prepared by mixing a high fat diet and an extract of the present invention in the same amount as daily dose of it. Precisely, an extract of the present invention prepared in the above Example 3 was so included in feed for an experimental group that a rat can take it as much as 5 ml/kg (for example, an adult weighing 60 kg of body weight may be daily administered with 300 ml of the extract, and a white rat weighing 200 g of body weight may be administered with 1 ml of the extract). In general, a white rat (about 200 g) takes 15 g of feed, so that 15 g of feed should include 1 ml of an extract of the present invention. Feed and water were provided freely. Weight changes were measured every 10 days for 33 days.

As a result, an average weight of a control group was increased by 37.3% after 33 days, in comparison to a normal diet group. An average weight of an experimental group was decreased by 15.3%, in comparison to a control group. As only increased weight was compared (the rate of weight increase of a control was considered as 100%), weight reduction effect shown by an experimental group was 59.3%, comparing to a control group (FIG. 1, Table 1). The above results indicate that an extract of the present invention can effectively control weight gain by high fat diet owing to its excellent weight loss effect.

TABLE 1

| Group | Initial weight (g) | Weight after 33 days (g) | Amount of weight gain (g) |
|---|---|---|---|
| Normal diet group | 171.25 ± 1.43 | 268.0 ± 2.04 | 96.75 ± 2.28 |
| High fat diet group | 170.0 ± 2.12 | 324.5 ± 5.05 | 154.5 ± 6.22 |
| High fat diet + extract of present invention (Experimental group) | 175.25 ± 2.28 | 306.25 ± 22.66 | 131.0 ± 22.09 |

Experimental Example 2

Analysis of Blood Lipid Levels

After 33 days of a dietary treatment, rats abstained from food for 12 hours and then anesthetized by ethyl ether to cut the abdomen open. Blood was taken with a disposable syringe from ventricle, which was centrifuged at 3,000 rpm for 20 minutes, resulting in a sample serum. The lipid contents of the serum, such as cholesterol, triglyceride, low-density lipoprotein (LDL) and high-density lipoprotein (HDL) were measured.

Figure 2:
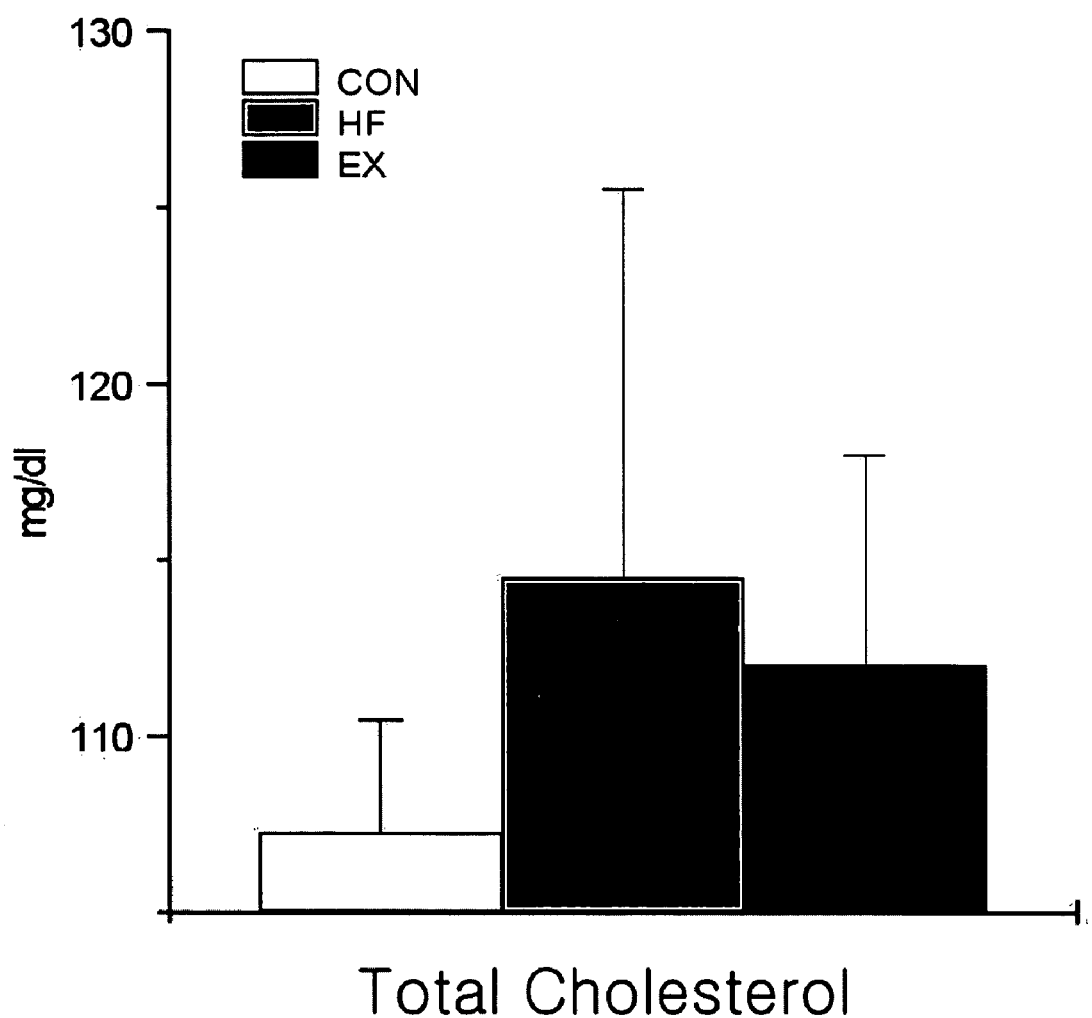
FIG. 2 is a graph showing the changes of cholesterol contents of each rat in a normal diet group, a high fat diet group (control group) and an experimental group fed with high fat diet together with an extract of the present invention, CON: Normal diet group, HF: High fat diet group (control group), EX: High fat diet+extract of the present invention
Figure 3:
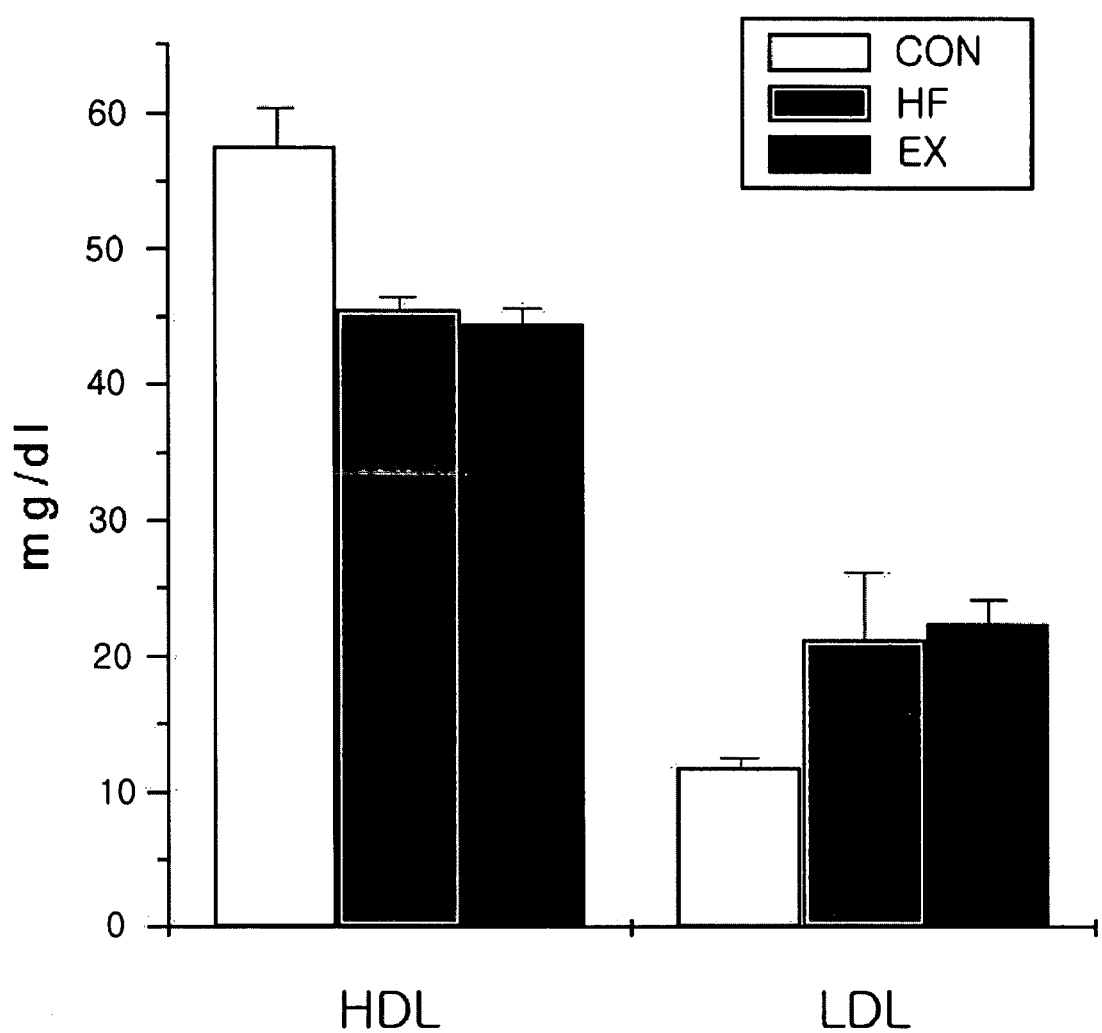
FIG. 3 is a graph showing the changes of HDL and LDL of each rat in a normal diet group, a high fat diet group (control group) and an experimental group fed with high fat diet together with an extract of the present invention, CON: Normal diet group, HF: High fat diet group (control group), EX: High fat diet+extract of the present invention
Figure 4:
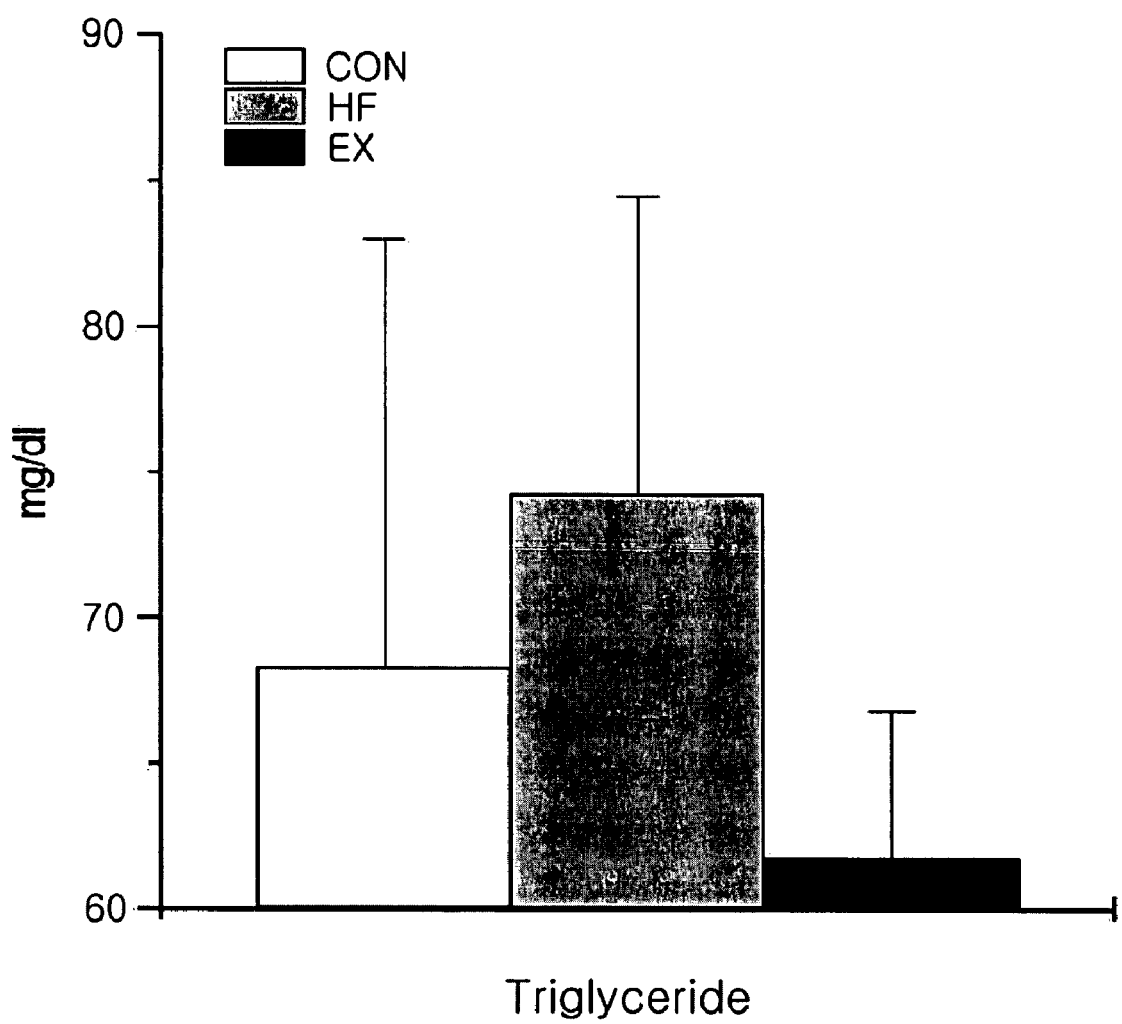
FIG. 4 is a graph showing the changes of triglyceride content of each rat in a normal diet group, a high fat diet group (control group) and an experimental group fed with high fat diet together with an extract of the present invention.

As a result, total cholesterol content of a control group was increased by 6.5% in comparison to a normal diet group. Total cholesterol content of an experimental group was, though, less increased than that of a control (FIG. 2). The contents of HDL and LDL were not significantly changed (FIG. 3). The content of triglyceride was increased by 8.8% in a control group, in comparison to a normal diet group. However, the content of triglyceride in an experimental group was decreased by 16.8%, in comparison to a control (FIG. 4). The results indicate that an extract of the present invention can effectively control the serum lipid level, which was increased by high fat diet, owing to its excellent neutral fat reduction effect. Further, the contents of glucose, alanine aminotransferase (ALT), aspartate aminotransferase (AST) and albumin in blood were additionally measured, but no significant changes were detected.

Experimental Example 3

Acute Toxicity Test in Rats Via Oral Administration 6-week old rats of a specific pathogen-free (SPF) SD line were used in the tests for acute toxicity. The rats were divided into three groups, which were a excipients control group administered with sterilized distilled water injection, an experimental group administered with 20 ml/kg and 40 ml/kg of the mixed herb extract and a positive control group administered with 13% ethanol. Each group consists of 5 animals. Death, clinical symptoms and weight change in rats were observed, hematological tests and biochemical tests of blood were performed, and any abnormal signs in the gastrointestinal organs of the chest and the abdomen were observed with eyes in autopsy. The results were as follows.
1. No death animal was reported during test period.
2. In aspect of general symptoms, walking difficulty, dorsal position, crawling position and disturbance of consciousness were observed until 6 hours after administration in a positive control and in an experimental group administered with over 20 ml/kg of the mixed herb extract.
3. According to autopsy statement, toxicological abnormalities related to the administration of the mixed herb extract were not observed.

In conclusion, the oral administration of the mixed herb extract of the present invention only caused general symptoms of alcohol intake in rats, which were recovered soon, and other toxicological changes were not observed.

And, no death animals were reported, indicating that the minimum lethal does (MLD) of the composition of the invention is over 40 ml/kg.

As explained hereinbefore, a mixed herb extract of the present invention inhibits obesity resulting from high fat diet and decreases total cholesterol and triglyceride. Thus, the extract of the invention can be effectively used as an auxiliary medicine for the prevention and treatment of obesity resulting from high fat diet, and might be further used as a weight reducer or a subsidiary agent for weight loss for the people who want to have a beautiful appearance.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An extract of an herbal mixture of cassia seeds (*Cassia obtusifolia* L.), green tea (*Thea sinensis* L.), eucommia bark (*Eucommia ulmoides* Oliver), garlic (*Allium sativum* var. *pekinense*), hawthorn (*Crataegus Pinnatifida* Bunge), fresh pine needle (*Pinus densiflora* Siebold et Zuccarini) and wormwood (*Artemisia capillaris* Thunberg) extracted by using water or aqueous alcohol solution.

2. The extract as set forth in claim 1, wherein the extract is prepared by hot-water extraction by adding water.

3. The extract as set forth in claim 1, wherein the aqueous alcohol solution is selected from a group consisting of 5–100% ethyl alcohol and 5–100% methyl alcohol.

4. The extract as set forth in claim 1, wherein the extract is fermented after adding rice, malt and yeast to the extract.

5. A pharmaceutical composition for the treatment of obesity containing the extract of claim 1 is an effective ingredient.

6. A health food for treatment of obesity containing the extract of claim 1 as an effective ingredient.

* * * * *